United States Patent [19]

Bullis, Jr.

[11] Patent Number: Plant 6,979

[45] Date of Patent: Aug. 8, 1989

[54] BROMELIACEAE PLANT

[76] Inventor: Harvey R. Bullis, Jr., 12420 SW. 248th St., Princeton, Fla. 33032

[21] Appl. No.: 219,648

[22] Filed: Jul. 15, 1988

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety of the Bromeliaceae family was developed as an inter-specific cross between *Aechmea dichlamydea* Baker var. trinitensis L. B. Smith and *A. fasciata* (Lindley) Baker var. fasciata and generally resembles the parent varieties but has leaves that lack the bars of the var. fasciata and have leaf sheaths that are wider, the scape bracts being less compactly positioned than those of the var. fasciata thus providing a more open inflorescence while the sepals exceed the floral bracts and provide a more attractive inflorescence. In contract to the var. trinitensis the leaf scales are whitish and translucent and the spiked are polystichously flowered instead of distichously flowered. The inflorescence is perceptively colored and many parts have areas that in color are dominated by a purplish pink, pink and/or purplish red hue, the petals of newly opened flowers having purplish white margins and a center field that in color is dominated by a violet hue and merges with color in the claw that is dominated by a purple hue while the petals of newly closed flowers are in color dominate by a red hue.

4 Drawing Sheets

1

The invention relates to a new and distinct plant variety of the Bromeliaceae or pineapple family and which was derived from the cross *Aechmea dichlamydea*×*fasciata* and has been named (cv) "Pink Frost" by the inventor.

The species *fasciata* of the genus Aechmea has been one of the more popular and sought after bromeliads for many years. Its popularity is due among other things to its beautifully proportioned vaselike form, its attractive green leaves which are barred with wide silver cross-bands, and to the striking pink, pyramidal inflorescence which is dotted with lavender blue flowers, the inflorescence having a relatively long life so that it remains a distinctive, colorful house decoration for many months. The variety 'fasciata' is one of the better known varieties and may be said to have green leaves which are barred with sivery white cross bands, the sheaths being slightly wider than the leaf blades. The scape-bracts present a rose coloration and are massed beneath the inflorescence. The inflorescence is considered compact, being about 7–8 cm long and the primary bracts and scape bracts exceed the branches while scapes exceed rose colored floral bracts.

The species *dichlamydea* of the genus Aechmea has not been as popular as some of the other bromeliads but the botanical variety 'trinitensis' is known in the trade for its large laxly compound inflorescence with bright red scape bracts and primary panicle bracts. The variety has gray green leaves with a brownish scale and marginal teeth up to 3 mm long. The spikes are flattened and distichously flowered and the sepals are up to 19 mm long.

The general objective of the invention has been to develop a new variety of bromeliad with an attractive inflorescence that is durable and retains its color for long periods.

The objectives of the invention have been fully realized by the development of the new plant variety described hereinafter in detail. The new plant variety was developed in a nursery located at Princeton, Fla., as a hybrid secured by cross-pollinating the flower of a plant

2 specimen of the variety 'trinitensis' of the species *dichlamydea* with pollen taken from a plant specimen of the variety 'fasciata' of the species *fasciata*. The seeds taken from the fertilized seed pod of the maternal variety were cultivated at the mentioned nursery location, and after prolonged observation of the seedlings, the hybridized plant was selected and asexually reproduced by the inventor at the mentioned nursery through the propagation of offshoots taken from the original hybrid plant.

Through successive propagations, it has been ascertained that specimens of the new plant variety generally resemble the parent varieties but are distinguishable from the parent varieties and from other related varieties known to the inventor by a growth habit which is evident in specimens propagated and grown under nursery conditions utilized in the growing of bromeliads at Princeton, Fla. was combining the following principal characteristics:

1. Leaves
   - (A) with parallel and obscure venation,
   - (B) with a length usually of 60–85 cm and a maximum width usually of 5–11 cm when originating in the median part of the stem,
   - (C) with a basal disk area that is substantially wider than the maximum width of the leaves in the midblade area,
   - (D) with a translucent whitish scale on the adaxial and abaxial sides of the blades,
   - (E) with a distal blade area that has an outer field with a color at anthesis that is usually dominated by a yellowish green, yellow green and/or olive green hue and a transitional zone proximally of the outer field and with a color that is usually dominated by a yellow green hue,
   - (F) with a basal disk area that in most leaves at anthesis has a field which in color is usually dominated by a yellow, greenish yellow and/or yellow green hue but which in some leaves occasionally shows color that is dominated by a purplish red, purplish pink, red, reddish purple and- /or pink hue and appears as a continuous color or as spots and blotches that frequently extend into the distal blade area, and (G) with marginal teeth that are usually 2.0–2.2 mm long at midleaf and in color at anthesis usually dominated by a brownish orange, orange, brown and/or yellow brown hue.

2. An inflorescence that has a 2–5 month life and:

(A) a scape (1) with a length of usually 30–45 cm (from insertion to the panicle), and (2) with color at anthesis that is usually dominated by a purplish pink and/or pink hue;

(B) scape-bracts (1) located at intervals of usually 20–35 mm in the area below the panicle, (2) with parallel and obscure venation, (3) with a length of usually 85–100 mm and maximum width of usually 17≧20 mm in the area below the panicle, and (4) with an acuminate tip area that in color is usually dominated by a greenish yellow and/or yellow green hue and a proximal area that in color is usually dominated by a purplish pink and/or purplish red hue;

(C) a panicle having: (1) a primary axis (a) with a length of usually 15–18 cm and a diameter of usually 8–12 mm, and (b) with a distal area at anthesis that in color is usually dominated by a yellow green hue and a base area at anthesis that in color is usually dominated by a pink and/or purplish pink hue, (2) primary bracts (a) with parallel and obscure venation, (b) with a length range at anthesis of 40–90 mm and a width range at anthesis of 6–20 mm and, (c) with an acuminate tip area that in color at anthesis is usually dominated by greenish yellow and/or yellow green and a proximal area that in color at anthesis is usually dominated by a purplish pink and/or purplish red hue, (3) primary branches (a) with an oval cross section, (b) with a length at anthesis of usually 75–120 mm including a length of usually 7–25 mm for the primary branch stipe, and (c) with color at anthesis on the adaxial sides of the stipes for the branches that is usually dominated by a purplish pink hue and color at anthesis on the abaxial side of the stipe for the branches that is usually dominated by a yellow green, green and/or yellow hue, (4) floriferous spikes (a) with a central axis that is triquetrous in cross section, (b) with a length at anthesis of usually 30–150 mm long and a diameter at anthesis of about 3–5 mm, and (c) with color at anthesis that is usually dominated by a yellow and/or yellow green hue, (5) floriferous bracts (a) with obscure venation, (b) with a length at anthesis of usually 15–28 mm and a maximum width at anthesis of usually 7–15 mm, and (c) with a distal area at anthesis which is dominated by a purplish pink hue and a proximal area which in the younger bracts is in color dominated by a yellow green hue, (6) sepals (a) with obscure parallel venation, (b) with a length at anthesis of usually 11–14 mm and a maximum width at anthesis of usually 5–7 mm, and (c) with a color at anthesis which is usually dominated by a purplish pink hue, (7) petals (a) with venation that is obscure in the proximal area and becomes dichotomous in the distal area, (b) with a length at anthesis of usually 17–20 mm and a maximum width at anthesis in the distal area of usually 6–7 mm, (c) with a distal area having a purplish white margins and a center field that in color is usually dominated by a violet hue and a claw having a color that is usually dominated by a purple hue when present in newly opened flowers, (d) with color dominated by a red hue when present in newly closed flowers.

The accompanying drawings serve, by color photographic means, to illustrate the new plant variety and wherein: One sheet shows a potted specimen that is about one year old from initial propagation of an approximately six week old offshoot; another sheet shows a close-up of the inflorescence on the potted specimen and at an early stage in the development thereof; another sheet generally shows the inflorescence at an advanced stage of maturity and with flowers in bloom; and the fourth sheet is a close-up of one of the spikes of the inflorescence and shows an open flower.

The following is a detailed description of the new plant variety with colors and hues, unless otherwise clearly indicated by the text through the absence of color notations, being named in accord with the ISCC-NBS method of designating colors (U.S. Department of Commerce, National Bureau of Standard, Circular 553, issued Nov. 1, 1955), the named colors being interpreted from color notations derived by comparison with the color specimens in "The Munsell Limit Color Cascase" and/or the "Neighboring Hues Edition" of the Munsell Book of Color, both published by the Munsell Color Company, Inc., of Baltimore, Md. The following description is further based on observations of well fertilized plant specimens that were 12–14 months old from initial propagation as offshoots of about 6 weeks in age and which were grown under 70% shaded conditions provided by shade cloth at Princeton, Fla. and wherein temperatures range from 75° to 105° F. during the summer months, from 45° to 80° F. during the winter months and are ambient during intervening periods.

DETAILED PLANT DESCRIPTION

Name: *Aechmea dichlamydea×fasciata* (cv) 'Pink Frost'.

Parentage:

I. *Maternal.—Aechmea dichlamydea* Baker var. *trinitensis* L. B. Smith.

II. *Paternal—Aechmea fasciata* (Lindley) Baker var. *fasciata.*

Classification:

I. *Botanic.*—Family: Bromeliaceae or pineapple. Subfamily: Bromelioideae. Genus: Aechmea. Subgenus: Platyaechmea. Species: *dichlamydea×fasciata.*

II. *Commercial.*—Bromeliad foliage plant.

Form: Epiphytic or terrestrial (in cultivation), with erecto-patent leaves from a subcylindric to funnel-form rosette surrounding a scapose paniculate inflorescence (during anthesis) and forming ascending basal rhizomes which become leafy and rootable offshoots.

Stems:

I. *General.*—Short, upright and sheathed by overlapping expanded leaf bases, each having a latent axillary bud.

II. *Stem texture.*—Glabrous and fleshy.

III. *Stem size.*—(A) Length (Above Soil Level): Usually 150–190 mm at anthesis. (B) Diameter (Intermediate Soil Level and Scape Insertion). — Usually 35–50 mm at anthesis.

IV. *Stem shape.*—Terete and tapered somewhat to a narrower diameter at soil level.

Leaves:

I. *General.*—Simple and sessile with sheathing leaf bases and with longer mature blades being reflexed.

II. *Leaf texture.*—(A) Upper Epidermis: Glabrous to the eye but with longitudinal rows, usually about 0.1–0.15 mm apart, of peltate, translucent, orbicular to ovate, irregularly dentate scales that are usually 0.14–0.17 mm in diameter and located at intervals of usually 0.2–0.4 mm. (B) Lower Epidermis: Glaucous to almost glabrous to the eye and with longitudinal rows of closely spaced to approximate scales with the same characteristics as those of the upper epidermis.

III. *Leaf arrangements.*—Alternate and rosulate.

IV. *Leaf margins.*—Plane with irregularly spaced, or occasionally doubled, and slightly antrorse to erect spinose teeth that are usually 3–6 mm apart at midleaf and gradually becoming more closely spaced apart and more in the range of 1.5–2.5 mm apart near the leaf tip, the teeth usually being 1.9–2.2 mm across the base and 2.0–2.2 mm high at midleaf.

V. *Leaf venation.*—Parallel and obscure.

VI. *Leaf shape.*—Ligulate from an ovate to orbicular sheathing base and with a broadly rounded, spinose erect to weakly recurved mucronate to cuspidate tip.

VII. *Leaf size (at anthesis).*—(A) Length: Usually between 60 and 85 cm for those originating in the median part of the stem with the erect innermost leaves of the vaginula usually being 20–30 cm, the length of the expanded basal disk (from insertion to the lowermost marginal teeth) usually ranging from about 10 to 18 cm. (B) Width: Usually 5–11 cm and averaging 7.5–8.5 cm in the midleaf area of the median leaves while the expanded basal disk usually has a maximum width of 12–15 cm. (C) Thickness: Usually 1.0–1.3 mm at the center of the midleaf area and tapering laterally to 0.25–0.4 mm at the margins while becoming slightly thinner near the tip and typically 0.9–1.2 mm at the center of the blade just below the rounding of the apex. The blade is even thinner in the middle of the basal disk area, and typically 0.5–0.7 mm and tapering laterally to a membranous margin of 0.1–0.3 mm thick.

VIII. *Leaf color (at anthesis).*—(A) General: Distal blade area with an outer field that in color is usually dominated by a yellowish green, yellow green and/or olive green hue that merges proximally with color in a transition zone that is usually dominated by a yellow green hue and, in turn, merges proximally with the field of the basal disk area. The field of the basal disk area is, in color, usually dominated by a yellow, yellow green and/or greenish yellow hue in most leaves but occasionally, in some leaves, color, which is dominated by a purplish red, reddish purple, red and/or pink hue, appears as a continuous color component or as spots or blotches in the field of the basal disk area and from which the color frequently extends distally of the disk area and into the distal blade area, the blade having marginal teeth which in color are dominated by orange, brownish orange, brown and/or yellowish brown hues. (B) Distal Leaf Blade Areas: Commonly dark yellowish green (10 GY 4/4), moderate yellow green (2.5 GY 5/6) (5 GY 5/6), moderate olive green (5 GY 4.4) (7.5 GY 4/4) and strong yellow green (5 GY 5/8) (5 GY/6/8) in the outer field and moderate yellow green (2.5 GY 7/6) (near 2.5 GY 6/7) (5 GY 7/6), light yellow green (5 GY 8/6) and strong yellow green (2.5 GY 7/8) in the transition zone. (C) Basal Disk Areas: Commonly moderate yellow green (2.5 GY 7/6) (2.5 GY 6/6) (5 GY 7/6), light yellow green (5 GY 8/6), strong yellow green (2.5 GY 7/8), moderate greenish yellow (10 Y 7.8), dark greenish yellow (10 Y 6/6) and/or deep greenish yellow (near 10 Y 6/8) pale yellow (near 2.5 Y 8.5/2) (2.5 Y 8.5/4) (near 5 Y 8/4) (5 Y 9/4) (5 Y 8.5/4), pale greenish yellow (7.5 Y 9/4) (near 7.5 Y 8/4) and light greenish yellow (near 7.5 Y 8/6) in the field of the basal disk area of most leaves. Commonly dark purplish red (5 RP 3/4), dark reddish purple (2.5 RP 3/4), grayish red (2.5 R 5/4) ) (2.5 R 5/6), light grayish purplish red (10 RP 6/4), grayish purplish red (10 RP 5/4) (10 RP 5/6), moderate purplish red (10 RP 5/8), dark pink (10 RP 6/6), moderate red (2.5 R 5/8) and/or grayish pink (10 RP 7/2) appearing as spots, blotches and/or as a continuous color component in the field of the disk area of some leaves. (D) Leaf Margin Area: Usually concolorous with the blade area proximate thereto, the teeth being commonly moderate orange (near 2.5 YR 6/10), brownish orange (near 2.5 YR 5/10) (near 5 YR 5/6), strong brown (5 YR 4/6) and/or strong yellowish brown (near 7.5 YR 5/6) (7.5 YR 5/8).

INFLORESCENCE:

I. *Form.*—Generally erect or ascending with an elongate scape bearing closely appressed bracts below an elevated panicle which is comprised of an axis and simple or once pinnate compressed branches with the axis and branch each terminating in a spike.

II. *Scape.*—(A) General: Terete with appressed, imbricate, oblong-lanceolate, alternate, scape-bracts, each having a reflexed spinose acuminate tip and spinose dentate margins. (B) Scape Texture: Floccose and fleshy. (C) Scape Shape: Terete and tapering distally to the primary axis of the panicle. (D) Scape Size: (1) Length. — Usually 30–45 cm to the lowermost branch of the panicle. (2) Diameter. — Usually 11–13 mm at area of emergence from the vaginula and 10–12 mm near the base of the panicle. (E) Scape Color: (1) General. — Color usually dominated by a purplish pink and/or pink hue. (2) Scape with Flocculae in place. — Commonly light purplish pink (8.5 RP 8.1/5.5) and/or light pink (9.1 RP 8.1/5.5). (3) Scape with Flocculae missing. — Commonly strong pink (2.4 R 7.3/8.9) and/or vivid pink (10 RP 6.9/11.4) (9.1 RP 6.9/11.1).

III. *Scape-bracts.*—(A) General: Sessile, simple, transversely inserted, appressed below and slightly recurved near the bract tips and located at internodal intervals of 20–35 mm in the area below the flowering branches. (B) Scape-bract Texture: Chartaceous and flocculose with the flocculae in longitudinal rows between the veins. (C) Scape-bract Shape: Oblong lanceolate from a transverse line of insertion. (D) Scape-bract Margins: Plane, spinose, denticulate in the distal three-quarters, the teeth being erect to weakly antrorse, and occasionally paired, and usually being spaced apart 1–2 mm, up to 1.0 mm wide at the base and averaging 1.1 mm in height (length). (E) Scape-bract Venation: Parallel and obscure. (F) Scape-bract Size (at anthesis): Usually 85–100 mm long and 17–20 mm wide in the area of emergence from the vaginula and up to the first inflorescence branch. (G) Scape-bract Color (At full bloom): (1) General. — The color in the acuminate tip area is usually dominated by a greenish yellow and/or yellow green hue and merges proximally with a proximal area color usually dominated by a purplish pink and/or purplish red hue. (2) Acuminate Tip Area. — Commonly pale greenish yellow (1.5 GY 9.1/4), light yellow green (2.9 GY 9/4.9), moderate greenish yellow (10 Y 7/6) (near 10 Y 8/6) (near 10 Y 8/8) and/or brilliant yellow green (2.5 GY 8.5/8) (2.5 GY 8/8). (3) Adaxial Side in Proximal Area. — Commonly pale purplish pink (7.5 RP 8.6/3.0), strong purplish pink (5.5 RP 7.1/10), dark purplish pink (5 RP 6/8), moderate purplish red (5 RP 5/8) (5 RP 5/10) and/or deep purplish pink (5 RP 6/10) with flocculae in place: Commonly strong purplish red (5 RP 5/12) (7.5 RP 5/12) and/or deep purplish pink (7.5 RP 6/10) with flocculae missing. (4) Abaxial Side in Proximal Area. — Commonly moderate purplish pink (5 RP 7/8) and/or deep purplish pink (5 RP 6/10) (7.5 RP 6/10) with flocculae in place. Commonly strong purplish red (5 RP 5/12) (7.5 RP 5/12), deep purplish pink (5 RP 6/10) and/or moderate purplish red (5 RP 5/10) (7.5 RP 5/10) with flocculae missing.

IV. *Panicle.*—(A) General: Comprises a terete primary axis that constitutes a continuation of the scape and bearing somewhat horizontally flattened simple or once pinnate branches with each branch subtended by a primary bract and terminating in an elongate spike of flowers. (B) Primary Axis: (1) Primary Axis Texture. — Floccose and fleshy. (2) Primary Axis Shape. — Terete and tapering distally to the base of the terminal spike. (3) Primary Axis Size. — (a) Length: Usually 15–18 cm from the lowermost primary bract of the panicle to the lowermost bract of the terminal spike. (b) Diameter: Usually 10–12 mm at the lowermost primary bract and diminishing distally to 8–11 mm at the base of the terminal spike. (4) Primary Axis Color. — (a) General: Color usually dominated by yellow green hue in distal area proximate to base of terminal spike and merging distally with color which is located in the base area of the panicle axis and dominated by a purplish pink and/or pink hue. (b) With Flocculae in Place: Commonly pale yellow green (2.1 GY 9.1/2.0) (3.7 GY 9.1/2.2) in the distal area. Commonly light purplish pink (8.5 RP 8.1/5.5) and/or light pink (9.1 RP 8.1/5.5) in the base area. (c) With Flocculae Missing: Commonly brilliant yellow green (5.7 GY 8.6/9.5) (4.1 GY 8.6/10.3) in the distal area. Commonly strong pink (2.4 R 7.3/8.9) and/or vivid pink (10 RP 6.9/11.1) (9.1 RP 6.9/11.1) in the base area. (C) Primary Inflorescence Bracts: (1) General. — Sessile, simple, transversely inserted, wide-spreading, subtending an inflorescence branch and spaced apart at progressively shorter internodal distances of usually 16–22 mm and 2–4 mm at the respective proximal and distal ends of the primary axis which are located below the terminal spike. (2) Primary bract Texture. — Chartaceous and flocculose with the flocculae in longitudinal rows between the veins. (3) Primary bract Shape. — Ovate to oblong lanceolate from a transverse line of insertion and with an acuminate tip. (4) Primary bract Margins. — Plane, spinose denticulate in the distal three quarters, the teeth being erect to slightly antrorse, occasionally paired and usually spaced apart 0.7–2.0 mm, being up to 1.0 mm wide at the base and averaging about 1.0 mm in height. (5) Primary bract Venation. — Parallel and obscure. (6) Primary bract Size (At anthesis). — Usually 85–90 mm long and 18–20 mm wide as subtending the lower branches and becoming progressively smaller in the distal region of the axis, usually being 40–60 mm long and 6–9 mm wide at the uppermost branches. (7) Primary bract Color (at anthesis). — (a) General: The color in the acuminate tip area is usually dominated by a greenish yellow and/or yellow green hue and merges proximally with color in the proximl area of the bract which is dominated by a purplish pink and/or purplish red hue. (b) Acuminate Tip Area: Commonly pale greenish yellow (1.5 GY 9.1/4), light yellow green (2.9 GY 9/4.9), moderate greenish yellow (10 Y 7/6) (near 10 Y 8/6), and/or brilliant yellow green (2.5 GY 8.5/8). (c) Proximal Area: Commonly pale purplish pink (7.5 RP 8.6/3.0), strong purplish pink (5.5 RP 7.1/10), dark purplish pink (5 RP 6/8), moderate purplish red (5 RP 5/8) (5 RP 5/10) and/or deep purplish pink (5 RP 6/10) with flocculae in place. Commonly strong purplish red (5 RP 5/12) (7.5 RP 5/12) and/or deep purplish pink (7.5 RP 6/10) with flocculae missing. (D) Inflorescence Branches: (1) General. — Simple or once pinnately branched with the secondary branch subtended by a transversely inserted secondary bract, transversely compressed terete at internodal distances ranging from about 16–22 mm in the lower area of the axis to about 2–4 mm in the upper area of the axis below the terminal spike, each branch bearing sessile flowers arranged in a spike distal to the branch stipe. (2) Branch Texture. — Floccose and fleshy. (3) Branch Shape. — Compressed terete so as to be oval in cross-section, transversely oriented, and bearing transversely inserted bracts at the base of secondary branches and flowers. (4) Branch Size. — (a) Length: Usually 105–120 mm in the lower half of the panicle and usually 75–105 in the upper half of the panicle for the primary branches. The smaller basally placed and lateral or secondary branches usually being 35–70 mm in length during full bloom. (b) Diameter (Stipe Region): Usually 4.0–6.5 mm wide and 3.0 to 4.5 mm thick near the base of the primary branches and usually 3.0–4.5 mm wide and 2.5–3.5 mm thick near the branch origin for the smaller basally placed and lateral secondary branch stipes. (c) Length of Primary Branch Stipe to First Bract: Usually 15–25 mm for lower branches and diminishing to 7–12 mm for upper branches. (d) Length of Basally placed Branch Stipe to First Bract: Usually 15–20 mm where such branches are present. (e) Length of Lateral Secondary Branch Stipe to First Bract: Usually 3–9 mm at full bloom. (5) Branch Color (Stipe Color). — (a) General: Color on adaxial side of stipe is usually dominated by a purplish pink hue while color on the abaxial side of the stipe is usually dominated by a yellow green, and/or yellow hue. (b) With Flocculae Present: Commonly pale yellow green (2.5 GY 9/2) (5 GY 9/2) (10 Y 9/2) on the abaxial side and light purplish pink (7.5 RP 8/6) and/or pale purplish pink (7.5 RP 8/4) (7.5 RP 9/2) on the adaxial side. (c) With Flocculae Missing: Commonly pale yellow (near 5 Y 9/2) (near 7.5 Y 9/2) on the abaxial side and deep purplish pink (7.5 RP 6/10), moderate purplish pink (7.5 RP 7/8), and/or light purplish pink (7.5 RP 8/6) (RP 8/6) on the adaxial side. (E) Floriferous Spikes: (1) General. — Terminal on each compressed terete polystichous inflorescence branch with a central axis triquetrous in cross-section and bearing sessile, imbricate, erecto-patent flowers, each spike being subtended by a partially sheathing entire-margined bract and each spike displaying one open flower at a time. (2) Spike Axis Texture. — Floccose on the ridges and efloccose on flattended unexposed surfaces and fleshy. (3) Spike Axis Shape. — Three angles in cross section with rounded ridges and flattened faces opposite each appressed flower. (4) Spike Axis Size. — Usually 85–110 mm long on primary branches, 30–75 mm long on secondary branches and 125–150 mm long on the terminal spike while the diameter is usually 3–5 mm when in full bloom. (5) Spike Axis Color (at anthesis). — (a) General: Usually dominated by a yellow and/or yellow green hue with flowers removed. (b) Commonly pale yellow (5 Y 9/2) (7.5 Y 9/2) and/or pale yellow green (10 Y 9/2) with flowers removed. (F) Floriferous Bracts (Spike Bracts): (1) General. — Sessile, single, transversely inserted, deeply concave and subtending a single sessile flower and located at approximately equal internodal distances of usually 3–4 mm throughout the spike. (2) Spike bract Texture. — Chartaceous and floccose and becoming glabrous with the loss of flocculae. (3) Spike bract Shape. — Broadly ovate with asymmetric tendencies from a transversely inserted base and deeply concave with a minutely denticulate margin and a spinose cuspidate tip, the venation being obscure. (4) Spike bract Size (When Flattened). — Usually 20–28 mm long and 12–15 mm maximum width for bracts located in the lower part of the spike and diminishing distally to bracts usually 15–18 mm long and 70–10 mm in maximum width in the distal part of the spike at anthesis. (5) Spike bract Color. — (a) General: Color in the distal area which is dominated by a purplish pink hue and which, in the younger bracts, merges proximally with color in the proximal area that is dominated by a yellow green hue. (b) With Flocculae Present: Commonly moderate purplish pink (5 RP 7/6), grayish purplish pink (5 RP 7/4), pale purplish pink (2.5 RP 8/4) and/or light purplish pink (2.5 RP 8/6) in the distal areas and with the color merging proximally with pale yellow green (2.5 GY 9/2) (10 Y 9/2) in the proximal areas of the younger bracts. (c) With Flocculae Missing: Commonly strong purplish pink (2.5 RP 7.10), deep purplish pink (2.5 RP 6/10) (5 RP 6/10) and/or moderate purplish pink (5 RP 7/8) (7.5 RP 7/6) (7.5 RP 7/8) in the distal areas and with the color merging proximally with pale yellow green (2.5 GY 9/2) (10 Y 9/2) in the proximal areas of the younger bracts. (G) Flowers: (1) General. — Sessile, epigynous with a receptacle cup, actinomorphic and bisexual with a calyx having three imbricate sepals, a corolla having three petals that open for only a few hours, usually early in the day, and then close and remain in place with a darkened color, an androecium of three epipetalous stamens and three free stamens, a gynoecium with a tricarpellate inferior ovary with axile placentation bearing numerous whitish ovules and with a slender terete style tipped by a flared tripartite stigma. (2) Texture. — (a) Sepals: Floccose and stiffly chartaceous. (b) Petals: Glabrous and fleshy. (c) Stamens: Glabrous and fleshy filaments and anthers. (d) Pistil: Scattered flocculae on the overy tending to become contiguous distally, the ovary being fleshy, the style being glabrous and fleshy and bearing brushy fleshy stigmas. (3) Margins. — (a) Sepals: Entire and membranous. (b) Petals: Entire with tendencies to become minutely erose around the expanded tip. (4) Venation. — (a) Sepals: Obscurely parallel veined. (b) Petals: Obscurely parallel veined below and becoming dichotomous in the rounded flabellate distal area. (5) Shape. — (a) Sepals: Ovate from the transverse insertion and terminating abruptly in a stiff spinose mucro. (b) Petals: Spathulate from the transverse, internally hirtellous, insertion line to the ovary and weakly mucronate at the tip. (c) Stamens: Terete filaments which are abruptly curved to the insertion near the middle of the weakly four-lobed sagittate anthers. (d) Pistil (at anthesis): Semi-terete, somewhat flattened on the adaxial face and rounded on the abaxial face and with three shallow rounded grooves, each opposite a carpellary septum, the ovary being about as long as it is wide and the style emerging from the center of the receptacle cup formed by the top of the ovary as a slender weakly three ridged cylinder which splits into three short branches distally with each branch bearing a ligulate fringed and crisped stigma. (6) Size. — (a) Sepals: Usually 11–14 mm long and 5–7 mm maximum width. (b) Petals: Usually 17–20 mm long and 6–7 mm maximum width and approximately 4 mm wide across the claw. (c) Stamens: Free filaments usually extend 11–15 mm above the rim of the receptacle cup which is 3–4 mm deep. The adnate filaments are about equal in length to the free filaments and have an approximately 3–4 mm free distal end portion. The filaments usually have a diameter of 0.6–1.0 mm and the anthers are usually 6.5–7.5 mm long and about 0.9–1.1 mm in maximum width. (d) Pistil (at anthesis):

Usually 22–27 mm from base of the ovary to the tip of the stigma, the ovary being 5–8 mm high and approximately 6–9 mm in diameter at anthesis. The style is usually 16–22 mm long between the ovary and the stigma bearing branches and 0.25–0.35 in maximum diameter, the stigma bearing branches usually being 3–4 mm long with the stigma being about 3 mm long and 1 mm wide. (6) Color. — (a) Sepals: 1. General. — Color dominated by a purplish pink hue. 2. With Flocculae Present. — Commonly moderate purplish pink (5 RP 7/6), pale purplish pink (2.5 RP 8/4) and/or light purplish pink (2.5 RP 8/6). 3. With Flocculae Missing. — Commonly strong purplish pink (2.5 RP 7/10), moderate purplish pink (5 RP 7/8) (7.5 RP 7/6) (7.5 RP 7/8) and/or deep purplish pink (2.5 RP 6/10). (b) Petals: 1. General. — Petals of newly opened flowers usually have a purplish white and/or very pale purple margin and a center field in the distal area which, in color, is dominated by a violet hue and merges proximally with color in the claw that is dominated with a purple hue. Petals of newly closed flowers usually exhibit color dominated by a red hue. 2. Newly Opened Flowers. — Commonly purplish white (10 PB 9/1) and/or very pale purple (2.5 P 9/2) along the margins and light violet (10 PB 5/6) (10 PB 5/8) and/or moderate violet (10 PB 4/8) (10 PB 4/6) in the center field of the distal area. Commonly very pale purple (5 P 9/2) and/or purplish white (5 P 9/1) in the claw. 3. Newly Closed Flowers. — Commonly moderate purplish red (10 RP 4/8) (10 RP 4/10) and/or moderate red (2.5 R 4/10) (2.5 R 4/8). (c) Stamens: 1. Filament. — Commonly purplish white (4.9 P 8.7/1.4) and/or bluish white (8.2 PB 8.7/1.3). 2. Anthers. — Commonly pale greenish yellow (7.8 Y 9/4) and/or pale yellow (5 Y 8.8/4.4). (d) Pistil: 1. Ovary. — Commonly pale yellow green (5 GY 9/2) (7.5 GY 9/2) and/or light yellow green (5 GY 9/4 (7.5 GY 9/4). 2. Style and Stigma. — Commonly purplish white (4.9 P 8.7/1.4) and/or bluish white (8.2 PB 8.7/1.3).

The following is a general description of a specimen of the new plant variety that was grown in a nursery at Princeton, Fla. from a vegative offshoot, the description having been taken during the period of flowering and during the month of January.

Age of plant: 12 months from initial propagation of offshoot that was about 6 weeks old.

Plant height: 86 cm from soil to apex of terminal bloom cluster.

Plant diameter (A) *At base of rosette.*—13 cm.

(B) *At greatest natural reach of leaves.*—82 cm.

Stem:

(A) *Length.*—17 cm from soil to inflorescence origin.

(B) *Diameter.*—45 mm at soil level.

Leaves:

(A) *Number of leaves.*—21.

(B) *Length.*—Ranges from 85 to 50 cm, excepting four much reduced innermost leaves surrounding the central funnel-form cup around the scape, and averaging 75 cm.

(C) *Width.*—Ranges from 65 to 90 at the widest area distal to the sheathing base area and averaging 79 mm.

(D) *Thickness.*—Ranging from 1.0 to 1.3 mm and averaging 1.1 mm along the midline axis, and ranging from 0.25 to 0.4 mm and averaging 0.3 along the margins.

(E) *Color.*—(1) Distal Blade Area: Dark yellowish green (10 GY 4/4), moderate yellow green (5 GY 5/6) and moderate olive green (5 GY 4/4) (7.5 GY 4/4). (2) Marginal Teeth: Brownish orange (near 2.5 YR 5/10), strong yellowish brown (7.5 YR 5/8). (3) Basal Disk Area: (a) Center field. — Grayish purplish red (10 RP 5/4) (10 RP 5/6), grayish red (2.5 R 5/6), grayish pink (10 RP 7/2) and dark purplish red (5 RP 3/4). (b) Insertion Area. — Purple yellow (2.5 Y 8.5/4) (near 5 Y 8/4) (5 Y 8.5/4) and pale greenish yellow (7.5 Y 9/4).

Inflorescence:

(A) *Number of Inflorescences.*—1. (1) Number of Spikes in Panicle: (a) Terminal Spikes. — 1. (b) Primary Branch Spikes. — 19. (c) Secondary Branch Spikes. — 23. (2) Number of Flowers on Panicle Spikes: (a) Terminal Spike. — 27. (b) Primary Branch Spikes. — 13–19. (c) Secondary Brancy Spikes. — 5–12. (3) Total Number ob Flowers: 453.

(B) *Scape.*—(1) Length: 37 cm. (2) Diameter: 12 mm at the area of emergence from the vaginula and 11 mm at the base of the panicle. (3) Color: (a) Scape with Flocculae in Place. — Light purplish pink (8.5 RP 8.1/5.5) and light pink (9.1 RP 8.1/5.5). (b) Scape with Flocculae Missing. — Strong pink (2.4 R 7.3/8.9) and vivid pink (10 RP 6.9/11.4)

(C) *Scape bracts.*—(1) Number: 11. (2) Size of Bracts above the vaginula; (a) Length. — 89–96 mm and averaging 93 mm. (b) Width. — 18–20 mm and averaging 19 mm.

(D) *Panicle primary axis.*—(1) Size: (a) Length Excluding Terminal Spike. — 165 mm. strong pink (2.4 R 7.3/8.9) (b) Diameter. — 11 mm at the base of the panicle to 9.5 mm at the base of the terminal spike. (2) Color: (a) With Flocculae in Place. — Pale yellow green (2.1 GY 9.1/2.0) distally, merging proximally with light purplish pink (8.5 RP 8.1/5.5) near the base. (b) With Flocculae Missing. — Brilliant yellow green distally, (4.1 GY 8.6/10.3), merging proximally with strong pink (2.4 R 7.3/8.9) near the base.

(E) *Bracts of the primary panicle axis.*—(1) Size: (a) Length. — 30–92 mm and becoming progressively shorter distally on the axis. (2) Color: (a) Acuminate Tip Area. — Light yellow green (2.9 GY 9/4.9), moderate greenish yellow (10 Y 7/6) and brilliant yellow green (2.5 GY 8.5/8). (b) Proximal Area. — Pale purplish pink (7.5 RP 8.6/3.0), strong purplish pink (5.5 RP 7.1/10) and moderate purplish red (5 RP 5/8) with flocculae in place and strong purplish red (5 RP 5/12) and deep purplish pink (7.5 RP 6/10) with flocculae missing.

(F) *Panicle terminal spike.*—(1) Size: (a) Length. — 145 mm. (b) Diameter of the primary Axis at the lower most Bract of the Terminal Spike. — 9.5 mm. (2) Color of Primary Axis at the Lowermost Bract of the Terminal Spike. — Pale yellow green (2.1 GY 9.1/2.0) (3.7 GY 9.1/2.2) with flocculae in place and brilliant yellow green (5.7 GY 8.6/9.5) with flocculae missing.

(G) *Panicle primary branches.*—(1) Stipes: (a) Length to the First Bract. — 6–20 mm. (b) Dimensions Near the Base of the Stipe. — 4–6.5 mm wide and 2.4 mm thick with the distal branches progressively smaller but retaining the same proportions in cross-section. (2) Primary Branch Spike. — (a) Length of the Flowering Spike: 65–95 mm with tendencies to be longer when secondary branches are lacking. (b) Diameter of the Spike Axis: 3–4 mm.

(H) *Panicle secondary branches.*—(1) Stipes: (a) Length from Base to First Bract. — 3–19 mm averaging 6 mm. (b) Dimensions Near the Base of the Stipe. — 3–4 mm wide and 2–3 mm thick. (2) Spikes: (a) Length of the Flowering Spike. — 30–60 mm with tendencies for basal branches to be longer. (b) Diameter of the Spike Axis, — 3–4 mm. (3) Spike Bracts Subtending Each Flower: (a) Length. — 15–28 mm becoming progressively shorter distally on the spike. (b) Width. — 7–13 mm becoming progressively narrower distally on the spike.

Flowers (When open and at maturity):

(A) *Length.*—From 25 to 35 mm and averaging 28 mm.

(B) *Diameter of calyx at midpoint.*—Varies from 5 to 7 mm.

(C) *Diameter of corolla at calyx midpoint.*—Varies from 3 to 4 mm.

(D) *Color.*—(1) Calyx: Moderate purplish pink (5 RP 7/6) and light purplish pink (2.5 RP 8/6) with flocculae present and strong purplish pink (2.5 RP 7/10) and moderate purplish pink (5 RP 7/8) (7.5 RP 7/6) with flocculae removed. (2) Corolla; Purplish white (10 PB 9/1) at the margins and moderate violet (10 PB 4/8) (10 PB 4/6) in the center field of the rounded distal area of the petals and very pale purple (5 P 9/2) and purplish white (5 P 9/1) in the claw.

I claim:

1. The new plant variety of the Bromeliaceae family as shown and described herein.

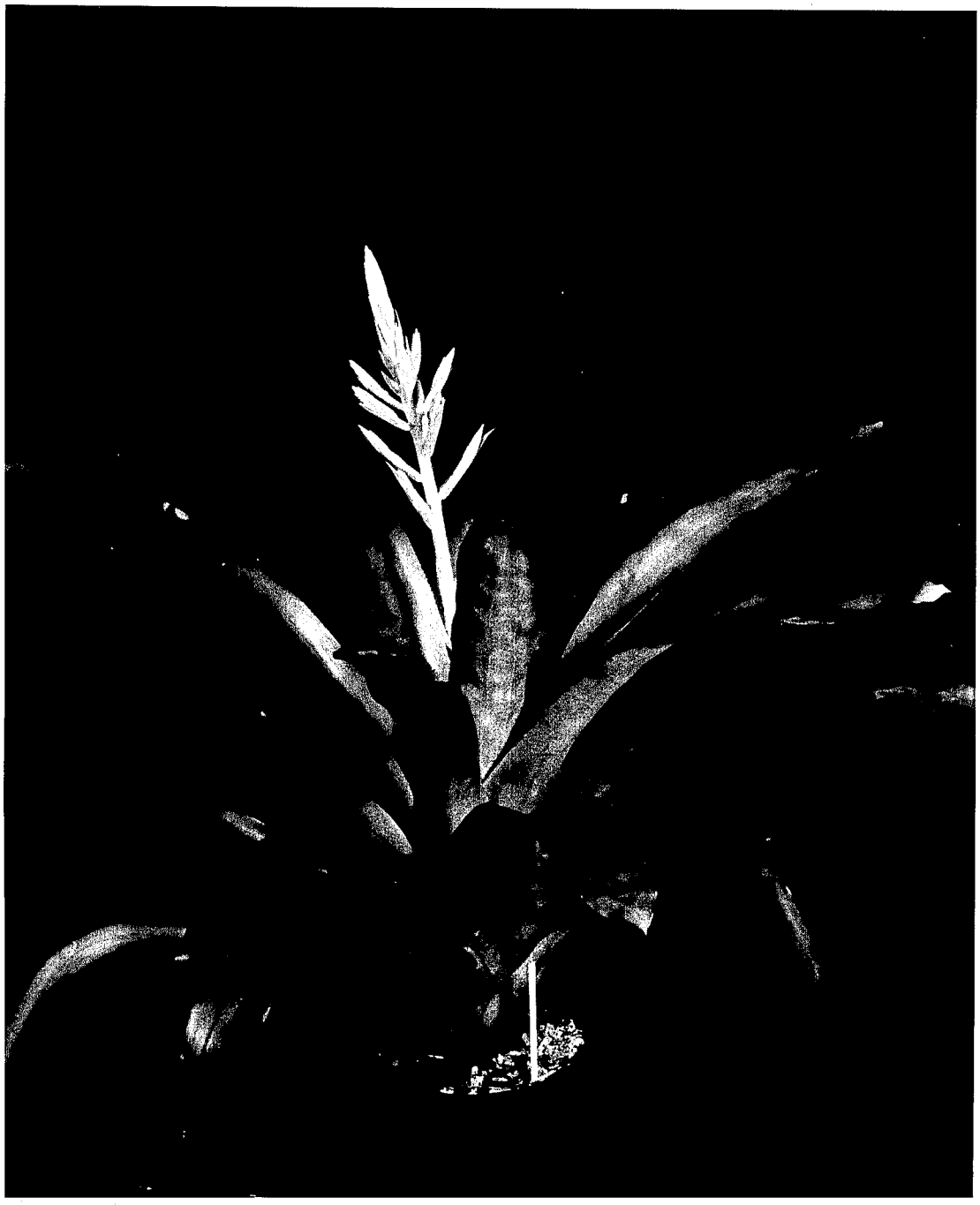

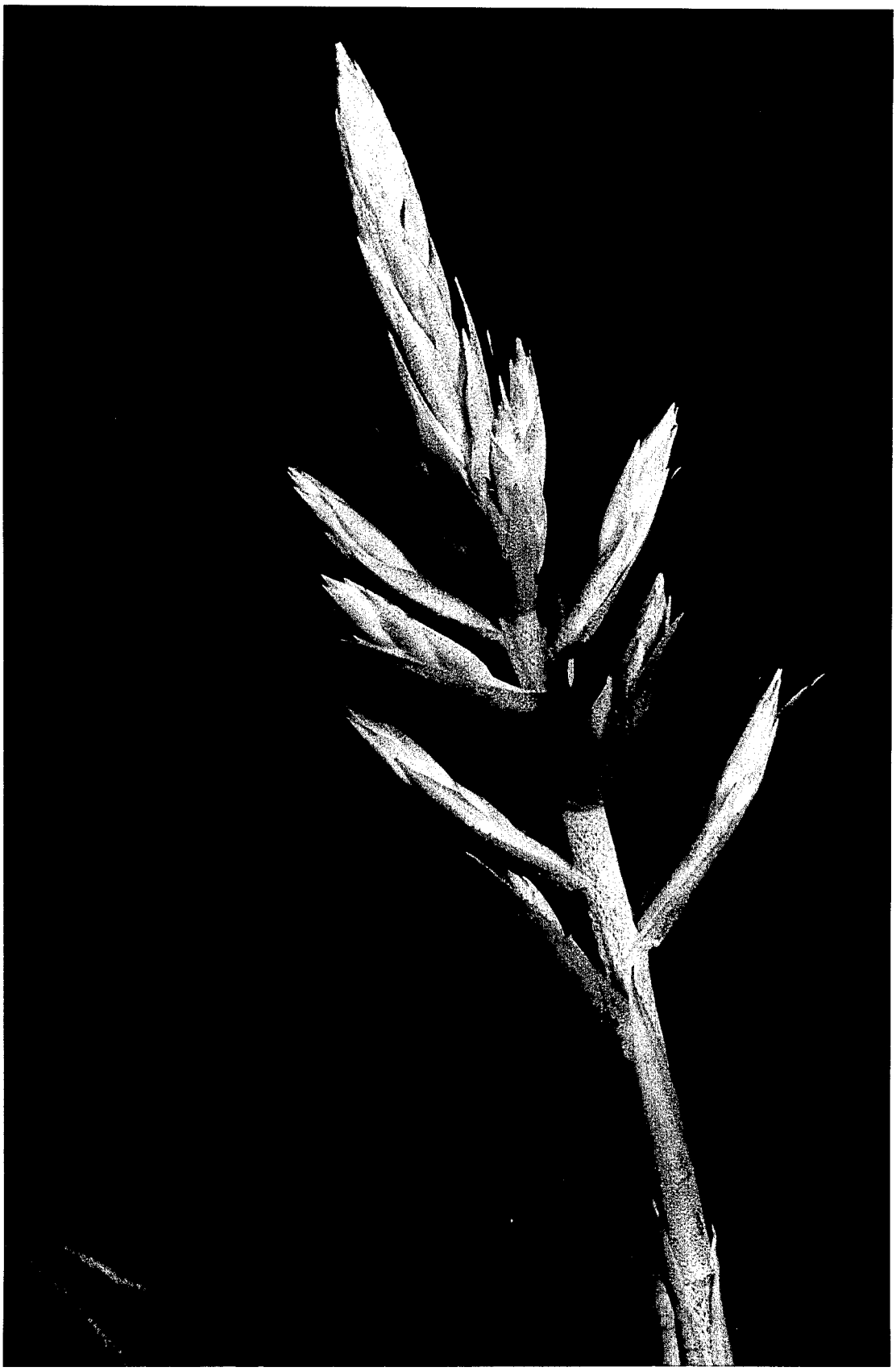

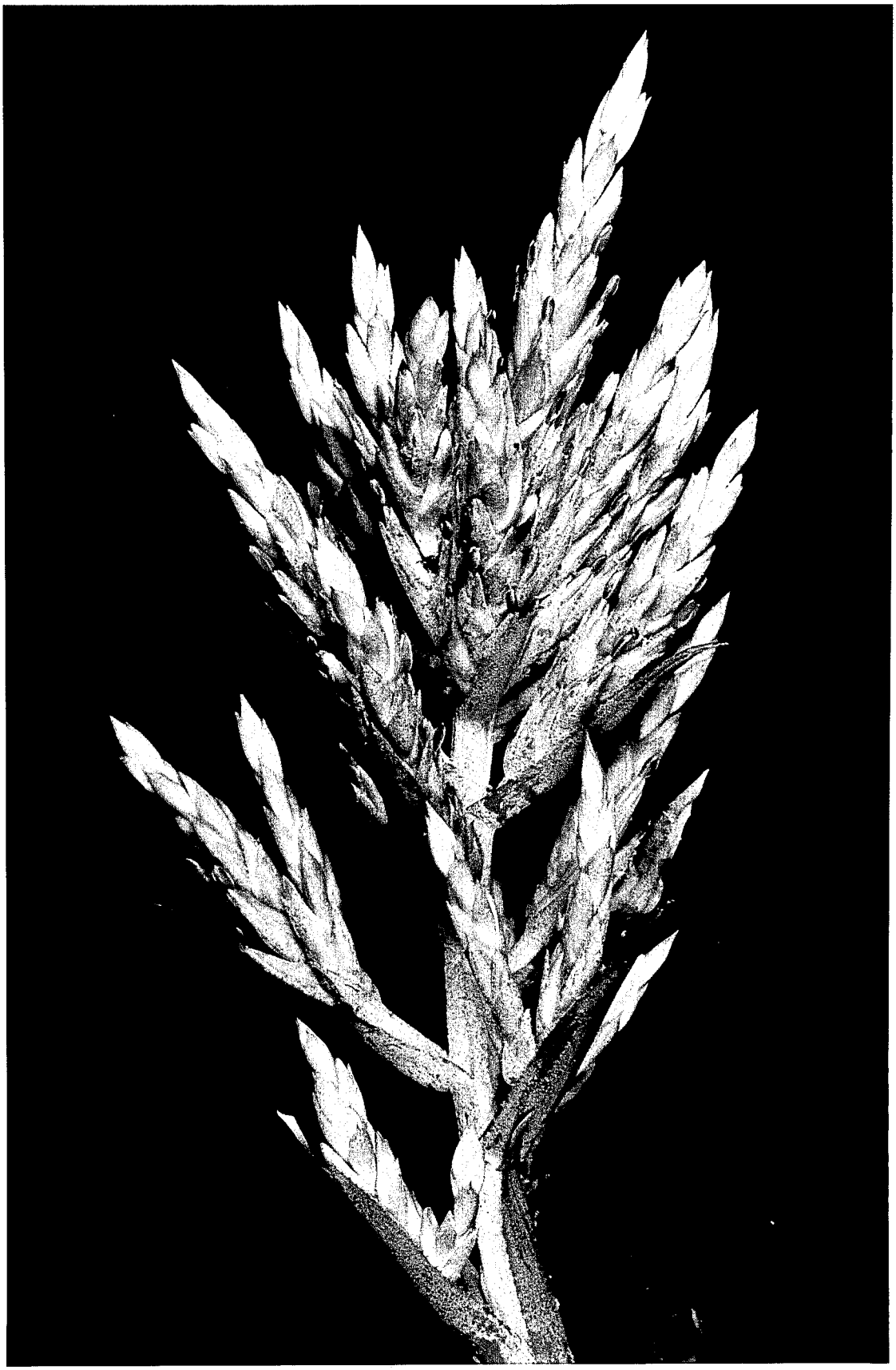

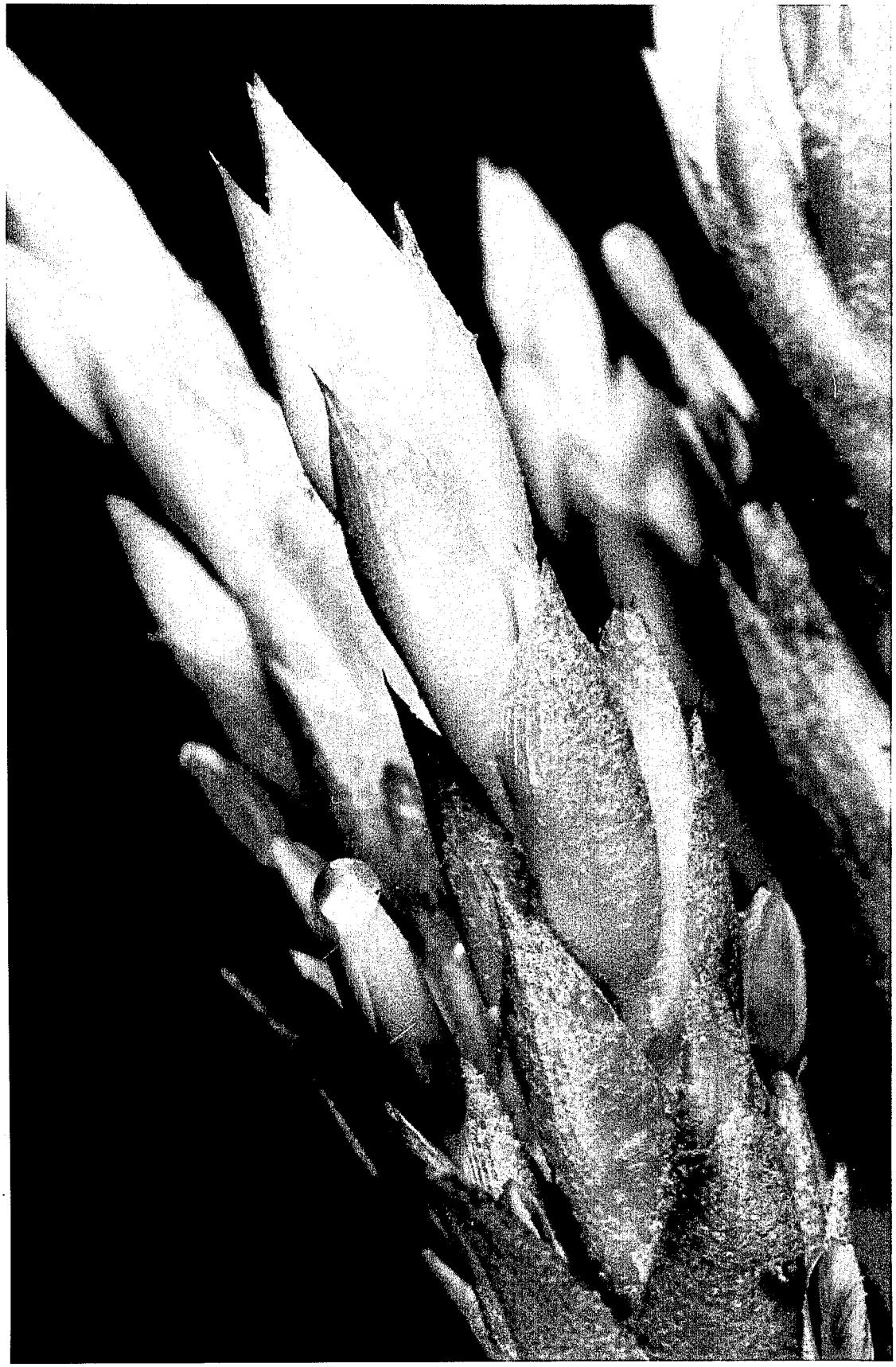

* * * * *